US005863739A

United States Patent [19]
LaRochelle et al.

[11] Patent Number: 5,863,739
[45] Date of Patent: Jan. 26, 1999

[54] ASSAY AND KIT FOR THE DETECTION OF α PLATELET DERIVED GROWTH FACTOR RECEPTOR

[75] Inventors: William J. LaRochelle, Gaithersburg; Jacalyn Pierce, Potomac, both of Md.; Roy A. Jensen, Franklin, Tenn.; Stuart A. Aaronson, New York, N.Y.

[73] Assignee: The United States of America as represented by the Department of Health and Human Services, Washington, D.C.

[21] Appl. No.: 460,069

[22] Filed: Jun. 2, 1995

Related U.S. Application Data

[60] Division of Ser. No. 81,216, Jun. 25, 1993, Pat. No. 5,468,468, which is a continuation-in-part of Ser. No. 915,884, Jul. 20, 1992, abandoned, which is a continuation of Ser. No. 308,282, Feb. 9, 1989, abandoned.

[51] Int. Cl.$^6$ ............................ G01N 33/53; C07K 16/28
[52] U.S. Cl. ....................... 435/7.2; 435/7.1; 530/388.22
[58] Field of Search ................. 435/7.1, 7.2; 530/388.22

[56] References Cited

U.S. PATENT DOCUMENTS

| 5,094,941 | 3/1992 | Hart . | |
| 5,268,358 | 12/1993 | Fretto | 514/12 |
| 5,371,205 | 12/1994 | Kelly et al. | 536/235 |

FOREIGN PATENT DOCUMENTS

| WO 90/10013 | 9/1990 | WIPO . |
| WO 93/11223 | 6/1993 | WIPO . |

OTHER PUBLICATIONS

Ashmun et al., "Monoclonal Antibodies to the Human CSF–1 Receptor (c–fms Proto–Oncogene Product) Detect Epitopes on Normal Mononuclear Phagocytes and on Human Myeloid Leukemic Blast Cells," *Blood* 73(3): 827–837 (1989).
Chaudry et al., "Expression of PDGF and Its Receptor in Neuroendocrine Tumors of the Digestive System," *Cancer Res.* 52: 1006–1012 (1992).
Hart et al., "Synthesis, Phosphorylation, and Degradation of Multiple Forms of the Platelet–derived Growth Factor Receptor Studied Using a Monoclonal Antibody," *J. Biol. Chem.* 262(22): 10780–10785 (1987).
Kawahara et al., "Monoclonal Antibody C3.1 is a Platelet Derived Growth Factor (PDGF) Antagonist," *Biochem. Biophys. Res. Comm.*, 147(2); 839–845 (1987).
LaRochelle et al., "Immunochemical Localization of the Epitope for a Monoclonal Antibody that Neutralizes Human Platelet–Derived Growth Factor Mitogenic Activity," *Mol. Cell. Biol.*, 9(8): 3538–3542 (1989).
Matsui et al., "Independent expression of human α or β platelet–derived growth factor receptor cDNAs in a naive hematopoietic cell leads to functional coupling with mitogenic and chemotactic signaling pathways," *P.N.A.S.*, USA 86: 8314–8318 (1989).
Ronnstrand et al., "Characterization of Two Monoclonal Antibodies Reactive with the External Domain of the Platelet–derived Growth Factor Receptor," *J. Biol. Chem.* 263(21): 10429–10435 (1988).
Seifert et al., "Two Different Subunits Associate to Create Isoform–specific Platelet–derived Growth Factor Receptors," *J. Biol. Chem.* 264(15): 8771–8778 (1989).
Vassbotn et al., "A monoclonal antibody against PDGF B–chain inhibits PDGF–induced DNA synthesis in C3H fibroblasts and prevents binding of PDFG to its receptor," *Biochem. Biophys. Acta*, 1054: 246–249 (1990).
Tiesman et al., "Identification Of A Soluble Receptor For Platelet–Derived Growth Factor In Cell–. . . ", *Journal of Biological Chemistry*, 268:13;9621–28, May 1993.
Krane et al., "Increased Dermal Expression Of Platelet–Derived Growth Factor Receptors In Growth–. . . ", *Journal of Investigative Dermatology*, 96:6;983–86, Jun. 1991.
Eccleston et al., "Expression Of Platelet–Derived Growth Factor (PDGF) And PDGF α–And β–Receptors. . . ", *Developmental Biology*, 155:2;459–70, Feb. 1993.
Yu et al., "Structural Coincidence Of αPDGF Epitopes Binding To Platelet–Derived Growth Factor–. . . ", *Journal of Biological Chemistry*, 269:1410668–674, Apr. 1994.
Queen, C. et al., PNAS, vol. 86:10029–10033, Dec. 1989.
Biotechnology News, vol. 13(5):7, Feb. 25, 1993.
LaRochelle, W.J., Inhibition of Platelet–Derived Growth Factor Autocrine Growth Stimulation By A vol. Monoclonal Antibody To The Human α Platelet–Derived Growth Factor Receptor Cell Growth & Differentiation, 4:547–553, Jul. 1993.
Huston, J.S. et al., Immunotechnology pub. Portland Press, pp. 47–60, (1993).
Morrison, S.L. et al., PNAS, vol. 81:6851–6855, Nov. 1984.
Claesson–Welsh, L. et al, Mol & Cel Biol, 8(8):3476–3486, Aug. 1988.
Bishayee, S. et al, Mol & Cel Biol, 8(9):3696–3702, Sep. 1988.
Heldin, Carl–Henrik et al, EMBO Journal, 7(5):1387–1393, 1988.
Hart et al., "Two Classes of PDGF Receptor Recognize Different Isoforms of PDGF" Science, 240: 1529–1531 (1988).

(List continued on next page.)

*Primary Examiner*—Susan A. Loring
*Attorney, Agent, or Firm*—Needle & Rosenberg, P.C.

[57] ABSTRACT

Potent neutralizing monoclonal antibodies to the human α PDGF receptor (α PDGFR) and fragments thereof are described. These monoclonal antibodies specifically bind to an epitope on α PDGFR, inhibits PDGF binding with PDGF, antagonizes PDGF, and does not bind β PDGFR receptor. A hybridoma cell line producing such a monoclonal antibody, methods of in vivo imaging of a pathological conditions and methods of inhibiting the growth of a neoplasia expressing α PDGFR, which use these monoclonal antibodies are also described. In vitro assays for detecting the presence of α PDGFR and for evaluating the binding affinity of a test compound are also described.

2 Claims, 6 Drawing Sheets

OTHER PUBLICATIONS

Classon–Welsh et al. Identification and Structural Analysis of the A Type Receptor for Platelet–derived Growth Factor, *J. Biol. Chem.*, 264: 1742–1747 (1989).

Nister et al. "Expression of Messenger RNAs for Platelet–derived Growth Factor and Transforming Growth Factor –α and Their Receptors in Human Malignant Glioma Lines," Can. Res., 48: 3910–3918 (1988).

Matsui et al., "Independent Expression of Human α or β Platelet–Derived Growth Factor Receptor cDNAs in a naive Hematopoietic Cell Leads to Functional Coupling with Mitogenic and Chemotactic Signaling Pathways,"PNAS, 86: 8314–8318 (1989).

Williams et al., "Signal Transduction by the Platelet–Derived Growth Factor Receptor," *Cold Spring Harbor Symposium*, (1988).

ASSAY AND KIT FOR THE DETECTION OF α PLATELET DERIVED GROWTH FACTOR RECEPTOR

CROSS REFERENCE TO RELATED APPLICATIONS

This application is a divisional of application Ser. No. 08/081,216, filed on Jun. 25, 1993, now U.S. Pat. No. 5,468,468 which is a CIP of Ser. No. 07/915,884, filed Jul. 20, 1992 now abandoned, which is a continuation of U.S. patent application Ser. No. 07/308,282, filed Feb. 9, 1989, now abandoned. These related applications are herein incorporated by reference.

BACKGROUND OF THE INVENTION

Platelet-derived growth factor (PDGF) is a major serum mitogen for cells of mesenchymal origin such as glial cells, fibroblasts, and smooth muscle cells (Heldin, et al., *Cell Reg.* 1: 555–566 (1990); Aaronson, S., *Science* 254; 1146–1153 (1991)). Biochemical evidence has established the existence in vivo of three PDGF isoforms; PDGF AA, PDGF BB, and PDGF AB (Johnson et al., *Biochem. Biophys. Res. Commun.* 104: 66–71 (1982)). PDGF BB is the human homologue of the v-sis oncogene product (Doolittle et al., *Science* 221: 275–277 (1983); Waterfield et al. *Nature* 304: 35–39 (1983); and Devare et al., *Proc. Nat'l Acad. Sci. USA* 80: 731–735 (1983)). Cell responsiveness to PDGF depends on signal transduction through cell surface α or β PDGF receptors ("PDGFR's") (Matsui et al. *Science* 243: 800–804 (1989); Claesson-Welsh, et al., *Proc. Nat'l Acad. Sci. USA* 86: 4917–4921 (1989); and Yarden et al., *Nature* 323: 226–232 (1986)). The α PDGFR is triggered by all PDGF isoforms, while the β PDGFR is activated by PDGF BB and to a lesser extent by PDGF AB (Matsui, et al. *Proc. Nat'l Acad. Sci. USA* 86: 8314–8318 (1989); Hart, et al. *Science* 240: 1529–1531 (1988); and Heldin, et al. *EMBO J.* 7: 1387–1393 (1988)).

In a previous study, expression vectors for the α and β PDGFR cDNAs were introduced into an IL-3 dependent murine hematopoietic cell line, 32D, which did not normally express these genes (Matsui, et al. supra (1989)). Data revealed that each receptor independently coupled with signal transduction pathways inherently present in these cells. Furthermore, both receptors induced a readily detectable mitogenic and chemotactic responses. Activation of either PDGFR stimulated inositol phospholipid metabolism and mobilization of Ca++.

Although PDGF's physiological role is associated with wound healing and development, the interactions of PDGF with its cognate PDGFR have been implicated in neoplasia (Nister et al. *J. Biol. Chem.* 266: 16755–16763 (1991) and Fleming et al., *Oncogene* 7: 1355–1359 (1992)), arteriosclerosis (Ross et al., *Science* 248: 1009–1012 (1990) and Ferns et al., *Science* 253: 1129–1132 (1991)). PDGF has also been identified in fibrotic diseases (Smits et al., *Am. J. Path.* 140: 639–648 (1992)) such as scleroderma (Gay et al., *J. Invest. Dermatol.* 92: 301–303 (1989)) and glomerulonephritis (Iida et al., *Proc. Natl. Acad. Sci. USA* 88: 6560–6564 (1991)).

Methods of isolating PDGF have involved the purification of PDGF from platelets as described in Johnsson et al., *Biochem. Biophys. Res. Comm.* 104: 66–74 (1982) and the development of antibodies against PDGF which are capable of detecting PDGF. For instance, Kelly et al. *EMBO J.* 4: 3399–3405 (1985) describe the production of polyclonal antibodies against PDGF but which are not capable of distinguishing the various isoforms of PDGF. Niman et al., *Nature* 307: 180–183 (1984) describe monoclonal antibodies raised against synthetic peptides derived from the amino terminal of the B-chain of PDGF which are not suitable for identifying intact, active forms of PDGF. U.S. Patent No. 5,094,941 describe the production of monoclonal antibodies which recognize native PDGF and distinguish the three isoforms of PDGF. Vassbotn et al., *Biochim. Biophy. Acta,* 1054: 246–249 (1990) disclosed the production of monoclonal antibody mab 6D11 against PDGF which bound PDGF B-B and PDGF A-B and blocked binding with PDGFR. La Rochelle et al., *Mol. Cell. Bio.,* 9: 3538–3542 (1989) discloses the production of monoclonal antibody, sis 1, which recognizes human PDGF-BB and human PDGF-AB and inhibits PDGF receptor binding and mitogenic activities of PDGF-BB and PDGF-AB.

Similarly, poly- and monoclonal antibodies have been used to detect PDGFR's. For instance, Chaudhry et al., *Cancer Research* 52: 1006–1012 (1992) discussed the use of polyclonal antibodies against the α PDGFR to study neuroendocrine tumors. Hart et al., *J. Biol. Chem.* 262: 10780–10785 (1987) and Seifert et al., *J. Biol. Chem.* 264: 8771–8778 (1989) both describe the production of monoclonal antibody PR7212 which binds to the β PDGFR. Kawahara et al., *Biochem. Biophys. Res. Comm.* 147: 839–845 (1987) discloses the production of monoclonal antibody C3.1, raised against NR6 cells, which contain about 200,000 to 400,000 PDGFR's per cell. Kawahara showed that C3.1 acts as an antagonist by blocking PDGF stimulated mitogenesis, but they did not indicate where C3.1 binds the PDGFR. Ronnstrand et al., *J. Biol. Chem.* 263: 10429–10435 (1988) describe two monoclonal antibodies, denoted PDGFR-B1 and PDGFR-B2, and FAB' fragments thereof, that react with the PDGF receptor. Both antibodies recognized the extracellular part of the receptor, but neither blocked the binding of $^{125}$I-PDGF. A commercially available monoclonal antibody against α PDGFR is PR292, produced by Genzyme Corp., Cambridge, Mass. (product no. 1264-00). Although this monoclonal antibody is specific for the α PDGFR, it does not inhibit PDGF binding with its receptor.

Thus, a need exists for a potent neutralizing monoclonal antibody directed toward α PDGFR. Such a monoclonal antibody would be a potent antagonist capable of controlling or interfering with PDGF dependent autocrine growth associated with neoplasias, arteriosclerosis, fibrotic diseases and other pathological diseases known to be associated with α PDGFR expression.

SUMMARY OF THE INVENTION

The present invention is based upon the discovery that by a particular approach to the production of monoclonal antibodies against α PDGFR, it is possible to obtain monoclonal antibodies characterized by previously unrealized specificity. That is, it has been discovered that, by immunizing mice with a murine hematopoietic cell transfectant that expresses human αPDGFR at the cell surface, monoclonal antibodies can be obtained that recognize an epitope specific to α PDGF receptor, inhibit PDGF binding with PDGF receptor, that antagonize PDGF and that do not bind β PDGF receptor. This specificity profile is not presaged by the properties of conventional anti-α PDGFR antibodies, which generally are not specific to α PDGFR, but rather bind β PDGFR as well, or are not PDGF antagonists.

Thus, the invention relates to monoclonal antibodies or fragments thereof which specifically binds to an epitope on α PDGF receptor, inhibits PDGF binding with PDGF receptor, antagonizes PDGF and does not bind β PDGF receptor.

In another embodiment, the invention relates to a hybridoma cell line which secretes such a monoclonal antibody.

In another embodiment, the invention relates to a pharmaceutical composition for in vivo imaging of a pathological condition that expresses αPDGF receptors comprising the above monoclonal antibody or fragment thereof which is labeled and which binds αPDGF receptor in vivo; and a pharmaceutically acceptable carrier.

The invention further relates to an in vivo method of imaging a pathological condition that express α PDGF receptors comprising the steps of:

(a) administering to a subject an imaging-effective amount of the above described monoclonal antibody of fragment thereof which is labeled and a pharmaceutically effective carrier; and (b) detecting the binding of the labeled monoclonal antibody to the αPDGF receptors in the pathological condition.

The invention further relates to a method of inhibiting the growth of neoplasia that express α PDGF receptors comprising contacting the neoplasia with a growth inhibitory amount of the above described monoclonal antibody or fragment thereof.

The invention further relates to an assay for the detection of α PDGF receptors in a sample comprising contacting the sample with the above described monoclonal antibody or fragment thereof which is labeled and detecting the binding of the α PDGF receptor in the sample with the monoclonal antibody or fragment thereof.

The invention further relates to a kit for determining the presence of α PDGF receptor in a sample comprising a container containing the above described monoclonal antibody or fragment thereof.

The invention further relates to a method of evaluating binding affinity of a test compound to α PDGF receptor, said method comprising the steps of:

(a) contacting a sample containing the receptor with
   (i) the above described monoclonal antibody or fragment thereof which is labeled; and
   (ii) the test compound; and (b) measuring the amount of bound monoclonal antibody or fragment thereof, the amount being inversely proportional to the amount of test compound which bound to the receptor.

The invention further relates to a method of producing the above monoclonal antibody by immunizing Balb/c mice with murine hematopoietic cell transfectants that express α PDGFR at the cell surface.

BRIEF DESCRIPTION OF DRAWINGS

FIGS. 1A and 1B show the characterization of immunochemical probes of the human α PDGF receptor. Monoclonal antibodies ("mab") αR1 (lane 1) and PR292 (lane 2), as well as, antipeptide sera Anti-PR1 (lane 4) and Anti-PR2 (lane 5) were used to immunoprecipitate the human α PDGFR (FIG. 1A). Control antibodies MOPC21 (lane 3) and normal sera (lane 6) were also used. In FIG. 1B, mabs αR1, PR292, and MOPC21 were titered in a solid phase Enzyme-linked immunosorbent assay ("ELISA") to determine relative α PDGFR binding affinities.

FIG. 2 shows interspecies immunoreactivity of mab αR1. Monoclonal antibody αR1 (lane 1) was tested for recognition of human, monkey, pig, dog, cat, rabbit, hamster, rat, and mouse fibroblast α PDGFRS. Anti-PR2 (lane 3), which detected all species was used as a positive control for each cell line while MOPC21 (lane 2) served as a negative control.

FIGS. 6A and 6B show identification of α PDGF receptors in human tumors by mab αR1 (FIG. 6A). α PDGFRs were immunoprecipitated from the A3243, A204, A1235 human tumor cell lines. Mab αR1 also immunoprecipitated α PDGFRs from M426 human embryonic lung fibroblasts. Mab αR1 failed to immunoprecipitate α PDGFRs from mouse NIH3T3 cells. MOPC21 (FIG. 6B) served as a negative control.

Table 1 shows monoclonal antibody αR1 inhibition of 32D transfectants expressing either PDGF AA or PDGF BB and the α PDGFR. 32D αR transfectants expressing either PDGF or 32D cells which were not αR transfectants were incubated with 50 ng/ml mab αR1 as described in Experimental Procedures. Cell growth was measured by $^3$H-thymidine uptake after two days. A representative experiment is shown.

DETAILED DESCRIPTION OF THE INVENTION

The present invention relates to a monoclonal antibody, and to fragments thereof, specific for α PDGFR, characterized in that it binds α PDGFR, inhibits PDGF binding with PDGFR, antagonizes PDGF, and does not bind β PDGFR. This antibody is further characterized as having half maximal binding affinity of 50 picomolar as measured by solid phase enzyme linked immunosorbent assay. Exemplary of such an antibody within the present invention is the monoclonal antibody designated αR1, produced by Mab αR1 hybridoma cell line having been deposited at the American Tissue Type Collection on Jun. 23, 1993 and having accession no. HB 11390. Applicants have discovered that this monoclonal antibody is a potent neutralizing monoclonal antibody directed toward the extracellular domain (domains 1–5) of the α PDGFR and that it exhibits broad species immunoreactivity for α PDGFRs in species as diverse as human and rabbit. Characterization of the αR1 epitope, which exemplifies the monoclonal antibody of this invention, revealed that it was unique to α PDGFR and was not present in β PDGFR. Biochemical analysis indicated that αR1 binding was independent of terminal glycosylation. Other studies have revealed that αR1 recognizes the α PDGFR by immunoblotting after nondenaturing polyacrylamide gel electrophoresis ("PAGE") but not denaturing PAGE. Thus, the epitope is conformational and not solely linear, in nature. αR1 is further characterized by having a half-maximal binding affinity of 50 picomolar, as measured by solid phase Enzyme linked immunosorbent assay.

Further studies of αR1 revealed that PDGF AA or BB effectively inhibited its in vitro interactions with the α PDGFR. Conversely, αR1 inhibited exogenous PDGF AAor α PDGFR. Conversely, αR1 inhibited exogenous PDGF AA- or BB-induced DNA synthesis by 32D αR transfectants. These findings are consistent with the conclusion that αR1 recognizes an epitope which spatially overlaps with the PDGF binding domain, rather than indirectly interfering with PDGF binding.

Further support derives from another mab, PR292, which also interacts with the α PDGFR extracellular domain, but fails to inhibit PDGF ligand binding.

The monoclonal antibody according to this invention includes any naturally or non-naturally occurring polypeptide having the binding specificity of αR1, that is, a polypeptide which binds to an epitope on αPDGF receptor, inhibits PDGF binding with PDGF receptor and antagonizes PDGF, but does not bind β PDGF. Preferably the monoclonal antibody or fragment thereof of the present invention binds to the linear or conformational epitope of extra cellular domain of human α PDGFR. Examples of such polypeptides include a half antibody molecule (a single heavy:light chain pair), or a fragment, such as the univalent fragments Fab or Fab' and the divalent fragment F(ab')2 ("FAB" meaning fragment antigen binding), that possess the same specificity for binding αPDGFR as αR1. A fragment, according to the present invention may also be a single chain Fv fragment produced by methods well known in the art. See Skerra et al. *Science* 240: 1038–1041 (1988) and King et al. *Biochemical J.* 290: 723–729 (1991), each of which is hereby incorporated by reference. The monoclonal of the present invention also includes a non-peptide compound which is a "mimetic," i.e. a compound that mimics the epitope binding site of αR1 but that is water soluble, resistant to proteolysis and non-immunogenic. Conformationally restricted cyclic organic peptides which mimic αR1 can be produced in accordance with method well known to the skilled artisan. See e.g., Saragovi, et al., *Science* 253: 792–795 (1991), hereby incorporated by reference. The monoclonal antibody of the present invention also includes anti-idiotypic antibodies produced by methods well-known to the art of the invention. See, e.g. Cozenza, Eur. *J. Immunol.* 6: 114 (1976) and Harlow et al., *Antibodies: A Laboratory Manual,* Cold Spring Harbor Publications pp. 726 (1988), each of which is hereby incorporated by reference.

The term "epitope" as used in describing this invention, includes any determinant responsible for the specific interaction with an antibody molecule. Epitopic determinants usually consist of chemically active surface groupings of molecules such as amino acids or sugar side chains and have specific three-dimensional structural characteristics, as well as specific charge characteristics.

The monoclonal antibody according to this invention also includes monoclonal antibody conjugates, which are for example, enzymes such as horseradish peroxidase, alkaline phosphatase, β-D-galactosidase, glucose oxidase, glucoamylase, carboanhydrase, acetyl-cholinesterase, lysozyme, malate dehydrogenase or glucose-6 phosphate dehydrogenase. Fluorescent markers are also suitable conjugates and include fluorescein, fluorochrome, rhodamine, and the like. In such conjugates, the monoclonal antibody of the invention is bound to the enzymes or fluorescent markers directly or by way of a spacer or linker group, such as ethylene-diaminetetraacetic acid (EDTA), diethylenetriaminepentaacetic acid (DPTA), or the like. Other conjugates include chemiluminescents such as luminal and imidizol and bioiluminescents such as luciferase and luciferin. Cytostatics are also applicable as conjugates for the monoclonal antibody of the present invention and include alkylating substances, such as mechlorethamine, triethylene phophoramide, triaziquone, camustine, semustine, methotrexate, mercaptopurine, cytarabine, fluorouracile, antibiotics such as actinomycine, and hormones and hormone antagonists such as coricosteroids,such as prednisone or progestins. The monoclonal antibody conjugate may be prepared by conjugating a cytotoxic substance containing either the intact toxin or the A-chain derived from it to the monoclonal antibody or fragment thereof, according to techniques well-known in the art. Chaudry et al. *J. Biol. Chem.* 268: 94379441 (1993); Sung et al. *Cancer Res.* 53: 2092–2099 (1993) and Selvaggi et al., *J. Immuno-therapy* 13: 201–207 (1993), each of which is hereby incorporated by reference.

In one embodiment, the monoclonal antibody of the invention or fragment thereof is conjugated to a detectable label that is a radioisotope, such as $^3$H, $^{125}$I, $^{131}$I $^{32}$P, $^{35}$S, $^{14}$C, $^{51}$Cr, $^{36}$Cl, $^{57}$Co, $^{58}$Co, $^{59}$Fe, $^{75}$Se, $^{152}$Eu, and $^{99m}$Tc which can be detected by known means such as gamma and scintillation counters, autoradiographs and the like.

The monoclonal antibody of the present invention may also be a monoclonal heteroconjugate, i.e., a hybrid of two or more antibody molecules. A suitable heteroconjugate includes, for instance, half of the αR1 monoclonal antibody or fragment thereof and half of another monoclonal antibody, which is specific for a surface molecule on an immune effector cell, such as an NK cell or a macrophage. See Kerr et al. *J. Immun.* 144: 4060–4067 (1990); Hsieh-Ma et al. *Cancer Res.* 52: 6832–6839 (1992), hereby incorporated by reference.

In another embodiment, the monoclonal antibody of the invention is a chimeric monoclonal antibody. In one approach, the chimeric monoclonal antibody is engineered by cloning recombinant DNA containing the promoter, leader, and variable-region sequences from a mouse αR1 gene and the constant-region exons of a human antibody gene. The antibody encoded by such a recombinant gene is a mouse-human chimera. Its antibody specificity is determined by the variable region derived from mouse DNA; its isotype, which is determined by the constant region, is derived from human DNA. See Verhoeyn et al. *BioEssays* 8: 74 (1988), hereby incorporated by reference.

In another embodiment, the monoclonal antibody of the present invention is a "humanized" monoclonal antibody, produced by techniques well-known in the art. Carter et al., *PNAS* 89: 4285–4289 (1992); Singer et al., *J. Immun.* 150: 2844–2857 (1992) and Mountain et al. *Biotechnol. Genet. Eng. Rev.* 10: 1–142 (1992), each of which is hereby incorporated by reference. That is, mouse complementary determining regions ("CDRs") are transferred from heavy and light V-chains of the mouse Ig into a human V-domain, followed by the replacement of some human residues in the framework regions of their murine counterparts. "Humanized" monoclonal antibodies in accordance with this invention are suitable for use in in vivo diagnostic and therapeutic methods.

Monoclonal antibodies can be produced in various ways using techniques well-understood by those having ordinary skill in the art. Details of these techniques are described in *Antibodies: A Laboratory Manual,* Harlow et al. Cold Spring Harbor Publications, p. 726 (1988), which is hereby incorporated by reference.

Efforts to elicit immune responses and generate monoclonal antibodies without time consuming protein purification steps have taken advantage of rodent fibroblast transfectants expressing such proteins as v-fms or the CSF-1 receptor Sherr, et al., *Blood* 73: 1786–1793 (1989), hereby incorporated by reference. Applicants discovered that 32D, a cell line capable of growth in suspension culture, is applicable to this approach. 32D cells expressing the α PDGFR developed high serum titers to the α PDGFR in the majority of immunized mice. Applicants also observed high serum transfectants. The fact that 32D cells grow in suspension allows the harvesting of such cells without use of agents that might destroy a surface exposed protein to which antibodies are to be elicited. Thus, this cell system was found to be generally applicable to the generation of monoclonal antibodies to foreign proteins expressed in 32D secretory pathways.

Generally, monoclonal antibodies according to the present invention are prepared by immunizing BALB/c mice intraperitoneally with 32D cell transfectants expressing the human α PDGFR, with a series of booster immunizations. The 32D cells are an interleukin 3 (IL-3)-dependent mouse hematopoietic cell line, described in Greenberger et al., *Proc. Nat'l Acad. Sci. USA* 80: 2931–2935 (1983). Mouse sera is titered against the baculovirus expressed human α PDGF receptor by solid phase ELISA and immunorecognition is confirmed by immunoprecipitation analysis. Spleens from the mice producing the highest antibody titer against the α PDGFR are fused with Sp2/0 myeloma cells. Hybridomas secreting immunoglobulins directed against the α PDGFR are selected by ELISA and cloned by limiting dilution. Thus, in one embodiment, the present invention relates to a hybridoma secreting a monoclonal antibody specific for α PDGFR characterized in that it binds α PDGFR, but not β PDGFR, and is capable of inhibiting PDGF binding with PDGFR as described in Examples 5 and 7. In particular, the hybridoma of the present invention secretes the monoclonal antibody designated αR1, having been deposited at the American Tissue Type Collection on Jun. 23, 1993 and having accession no. HB 11390. The hybridoma cell lines of the present invention are genetically stable, secrete monoclonal antibodies of the invention and can be activated from deep-frozen cultures by thawing and recloning.

The monoclonal antibodies and fragments thereof according to this invention are multiplied according to in vitro and in vivo methods well-known in the art. Multiplication in vitro is carried out in suitable culture media such as Dulbecco's Modified Eagle Medium or RPMI 1640 medium, optionally replenished by a mammalian serum such as fetal calf serum or trace elements and growth-sustaining supplements, e.g. feeder cells, such as normal mouse peritoneal exudate cells, spleen cells, bone marrow macrophages or the like. In vitro production provides relatively pure antibody preparations and allows scale-up to give large amounts of the desired antibodies. Techniques for large scale hybridoma cultivation under tissue culture conditions are known in the art and include homogenous suspension culture, e.g., in an airlift reactor or in a continuous stirrer reactor or immobilized or entrapped cell culture.

Large amounts of the monoclonal antibody of the present invention may also be obtained by multiplying hybridoma cells in vivo. Cell clones are injected into mammals which are histocompatible with the parent cells, e.g. syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the mammal.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer as supplied by Applied Biosystems, Multiple Peptide Systems, etc., or they may be produced manually, using techniques well known in the art. See Geysen, et al. *J. Immunol. Methods* 102: 259–274 (1978), hereby incorporated by reference.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced.

Radioactively labeled monoclonal antibodies of the present invention are produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-99m by ligand exchange process, for example, by reducing pertechnate with stannous solution, chelating the reduced technetium onto a Sephadex column and applying the antibody to this column or by direct labelling techniques, e.g. by incubating pertechnate, a reducing agent such as SNCl2, a buffer solution such as sodium-potassium phthalate solution, and the antibody.

Thus, in one embodiment, the invention relates to a pharmaceutical composition for in vivo imaging of a pathological condition that expresses αPDGF receptors comprising the monoclonal antibody or fragment thereof of of the invention which binds αPDGF receptor in vivo; and a pharmaceutically acceptable carrier.

In another embodiment, the invention relates to an in vivo method of imaging a pathological condition which expresses α PDGF receptors using the above pharmaceutical composition. Applicants have shown in Examples 2, 4 and 5 and in FIGS. 3 and 7 that αR1 selectively binds α PDGF receptor. Previous studies have demonstrated functional autocrine PDGF stimulation in certain human tumor cell lines. Nister, et al. *J. Biol. Chem.* 266: 16755–16763 (1991) and Fleming, et al. *Oncogene* 7: 1355–1359 (1992), hereby incorporated by reference. Moreover, expression of the α PDGFR gene has been documented in human malignancies including glioblastomas and astrocytomas. Nister et al., supra; Fleming et al., supra; and Fleming et al. *Cancer Res.* 52: 4550–4553 (1992). Similarly, PDGF has been implicated in certain pathological conditions including arteriosclerosis, arthritis, scleroderma, bone marrow fibrosis and keloids. Thus, with the discovery of αR1, applicants have also discovered an in vivo method of imaging a pathological conditions that express α PDGF receptors. Specifically, this method involves administering to a subject an imaging-effective amount of a detectably labeled monoclonal antibody or fragment thereof having the binding specificity of αR1, and a pharmaceutically effective carrier; and detecting the binding of the labeled monoclonal antibody to the αPDGF receptors in the pathological condition.

The term "pathological condition" refers to an abnormality or disease, as these terms are commonly used. The pathological conditions of the present invention are those which express α PDGF receptors, such as, arteriosclerosis, arthritis, scleroderma, bone marrow fibrosis and keloids.

The common medical meaning of the term "neoplasia" refers to "new cell growth" that results as a loss of responsiveness to normal growth controls. A neoplasia includes "tumors," which may be either benign or malignant.

By the term "expresses α PDGFR" is meant that α PDGFR is produced by cells associated with a specific pathological condition and that production can be detected by any known method, for instance, by a direct assays of mRNA transcript. For instance α PDGFRs are expressed in neoplasias such as glioblastomas, astrocytomas, osteosarcomas, fibrosarcomas and SSV-transformed cells. See, e.g., Fleming et al., *PNAS* 86: 8063–8067 (1989) and *Cancer Res.* 52: 4550–4553 (1992), hereby incorporated by reference.

The term "in vivo imaging" refers to any method which permits the detection of a labeled monoclonal antibody of the present invention or fragment thereof that specifically binds to the α PDGFR located in the subject's body. A "subject" is a mammal, preferably a human, and most preferably a human known to have a neoplasia that expresses α PDGF receptors.

An "imaging effective amount" means that the amount of the detectably labeled monoclonal antibody or fragment thereof administered is sufficient to enable detection of binding of the monoclonal antibody or fragment thereof to the α PDGF receptor.

Generally, the dosage of the detectably labeled monoclonal antibody or fragment thereof will vary depending on considerations such as age, condition, sex, and extent of disease in the patient, counterindications, if any, concomittant therapies and other variables, to be adjusted by a physician skilled in the art. Dosage can vary from 0.01 mg/kg to 2,000 mg/kg, preferably 0.1 mg/kg to 1,000 mg/kg.

As noted above, the present invention encompasses monoclonal antibody conjugates in which the conjugate may be a detectable label. For purposes of in vivo imaging, the type of detection instrument available is a major factor in selecting a given label. For instance, radioactive isotopes and paramagnetic isotopes are particularly suitable for in vivo imaging in the methods of the present invention. The type of instrument is used will guide the selection of the radionuclide. For instance, the radionuclide chosen must have a type of decay which is detectable for a given type of instrument. However, any conventional method for visualizing diagnostic imaging can be utilized in accordance with this invention.

Another factor to consider in selecting a radionuclide for in vivo diagnosis is that the half-life of a nuclide be long enough so that it is still detectable at the time of maximum uptake by the target, but short enough so that deleterious radiation upon the host, as well as background, is minimized. Ideally, a radionuclide used for in vivo imaging will lack a particulate emission, but produce a large number of photons in a 140–2000 keV range, which may be readily detected by conventional gamma cameras.

As discussed above in connection with the production of monoclonal conjugates, a radionuclide may be bound to an antibody either directly or indirectly by using an intermediary functional group. Intermediary functional groups which are often used to bind radioisotopes which exist as metallic ions to antibody are diethylenetri-aminepentaacetic acid (DTPA) and ethylene diaminetetracetic acid (EDTA). Examples of metallic ions suitable for use in this invention are $^{99m}Tc$, $^{123}I$, $^{131}I$ $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$.

In accordance with this invention, the monoclonal antibody or fragment thereof may be labeled by any of several techniques known to the art. See, e.g., Wagner et al., *J. Nucl. Med.* 20: 428 (1979) and Saha et al., *J. Nucl. Med.* 6: 542 (1976), hereby incorporated by reference.

The methods of the present invention may also use paramagnetic isotopes for purposes of in vivo detection. Elements particularly useful in Magnetic Resonance Imaging ("MRI") include $^{157}Gd$, $^{55}Mn$, $^{162}Dy$, $^{52}Cr$, and $^{56}Fe$.

Administration to the subject may be local or systemic and accomplished intravenously, intraarterially, via the spinal fluid or the like. Administration may also be intradermal or intracavitary, depending upon the body site under examination. After a sufficient time has lapsed for the monoclonal antibody or fragment thereof to bind with the αPDGFR, for example 30 minutes to 48 hours, the area of the subject under investigation is examined by routine imaging techniques such as MRI, SPECT, planar scintillation imaging and emerging imaging techniques, as well. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its decrease with time is then monitored and recorded. By comparing the results with data obtained from studies of clinically normal individuals, the presence and location of the neoplasm can be determined and monitored.

The pharmaceutical composition of the present invention are advantageously administered in the form of injectable compositions. A typical composition for such purpose comprises a pharmaceutically acceptable carrier. For instance, the composition may contain about 10 mg of human serum albumin and from about 20 to 200 micrograms of the labeled monoclonal antibody or fragment thereof per milliliter of phosphate buffer containing NaCl. Other pharmaceutically acceptable carriers include aqueous solutions, non-toxic excipients, including salts, preservatives, buffers and the like, as described, for instance, in *Reminington's Pharmaceutical Sciences,* 15th Ed. Easton: Mack Publishing Co. pp 1405–1412 and 1461–1487 (1975) and *The National Formulary XIV.,* 14th Ed. Washington: American Pharmaceutical Association (1975), the contents of which are hereby incorporated by reference. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art. See *Goodman and Gilman's The Pharmacological Basis for Therapeutics* (7th Ed.).

Particularly preferred pharmaceutical compositions of the present invention are those that, in addition to specifically binding the α PDGFR in vivo, are also non-toxic at appropriate dosage levels and have a satisfactory duration of effect.

In another embodiment, the invention relates to a method of inhibiting growth of neoplasia that expresss αPDGF receptors. More specifically, the invention relates to a method of inhibiting growth of a neoplasias by contacting the neoplasia with a growth inhibitory amount of a monoclonal antibody or fragment thereof which specifically binds to an epitope on α PDGF receptor, inhibits PDGF binding with PDGF receptor, antagonizes PDGF, but does not bind β PDGFR. In the preferred embodiment, the monoclonal antibody is αR1 or a fragment thereof.

"Inhibiting growth" refers to a slowing or altering in a negative manner progressive cell growth. Preferably, inhibition involves the complete arrest of cell division. Methods of testing inhibition and the determination of what is meant by a "growth inhibitory amount" involve in vitro experimental cell models, such as 32DαR cells or in vivo animal model systems. In animal model studies, human tumors known to express PDGF and PDGFR are transplanted into mice. Iodinated αR1 is administered and at certain time points, mice are sacrificed and the monoclonal antibody localized by counting various tissues as well as the tumor itself. If the monoclonal is localized to the tumor, the monoclonal is then tested for inhibition of tumor growth in another, different set of mice. If the tumor regresses, the procedure is repeated using human subjects having neoplasias expressing α PDGFR. See Colcher et al. *J. Natl. Cancer Inst.* 82: 1191–1197 (1990) and Colcher et al., *Cancer Res.* 48: 4597–4603 (1988), both of which are herein incorporated by reference.

The quantity of the monoclonal antibody of the present invention necessary for effective therapy will depend upon many different factors, including the means of administration, target site, physiological state of the patient, other medicants administered, etc. Thus treatment dosages should be titrated to optimize safety and efficacy. Typically, dosages used in vitro may provide useful guidance in the amounts useful for in situ administration of the monoclonal antibody, and as noted above, animal models may be used to determine effective dosages for treatment of particular disorders. Various considerations are described, e.g. in Gilman et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa., each of which is herein incorporated by reference. Methods of administration are discussed therein and include, oral, intravenous, intraperitoneal, or intra muscular administration, transdermal diffusion, and others. Pharmaceutically acceptable carriers include, water, saline, buffers, and other compounds described, e.g., in *Merck Index,* Merck & Co., Rahway, N.J. Because of the high affinity of binding of the monoclonal antibody of the present invention with α PDGFR, low dosages of pharmaceutical compositions for purposes of inhibiting neoplasia growth would be effective. Thus, dosage ranges would ordinarily be expected to be in amounts lower than 1 mM concentrations, typically less than 10 μM, usually less than about 100 nM, preferably less than about 10 pM (picomolar), and most preferably less than aobut 1 fM (femtomolar), with the appropriate carrier. Slow release formulations, or slow release apparatus may be utilized for continuous administration.

In another embodiment, the invention relates to an in vitro assay for the detection of αPDGFR in whatever kind of "sample" it may occur, such samples including fluid, semi-fluid or tissue samples, using the monoclonal antibody or fragment thereof of the invention. The assay can be a competitive or sandwich assay, or any assay well-known to the artisan which depends on the formation of an antibody-antigen immune complex. For purposes of this invention, the monoclonal antibody or fragment thereof can be immobilized or labeled. Many carriers are known to the skilled artisan to which the monoclonal antibody or fragments thereof of the present invention can be bound for immobilization. Where required, derivatization techniques can be used for immobilizing the monoclonal antibody or fragment thereof on a substrate. Well-known carriers include glass, polystyrene, polypropylene, polyethylene, dextran, nylon, amylases, natural and modified celluloses etc. The carrier can be either soluble or insoluble. Immunoassays encompassed by the present invention include, but are not limited to those described in U.S. Pat. Nos. 4,367,110 (double monoclonal antibody sandwich assay); Wide et al., Kirkham and Hunter, eds. *Radioimmunoassay Methods,* E. and S. Livingstone, Edinburgh (1970); U.S. Pat. No. 4,452,901 (western blot); Brown et al., *J. Biol. Chem.* 255: 4980–4983 (1980) (immunoprecipitation of labeled ligand); and Brooks et al., *Clin. Exp. Immunol.* 39: 477 (1980) (immunocytochemistry).

The monoclonal antibodies and fragments thereof of the present invention may be used in in vitro assays designed to screen compounds for binding affinity to α PDGFR. See Fodor et al. *Science* 251: 767–773 (1991), incorporated herein by reference. Thus, the present invention contemplates a competitive drug screening assay, where the monoclonal antibodies or fragments thereof of the invention compete with a test compound for binding to α PDGFR. In this manner the monoclonal antibodies and fragments thereof are used to detect the presence of any polypeptide which shares one or more binding sites of the α PDGFR and can be used to occupy binding sites on the receptor which might otherwise be occupied by PDGF or a PDGF-like peptide.

In vitro assays in accordance with the present invention also include the use of isolated membranes from cells expressing a recombinant α PDGFR, soluble fragments comprising the ligand binding (PDGF) segments of α PDGFR, or fragments attached to solid phase substrates. These assays allow for the diagnostic determination of the effects of either binding segment mutations and modifications, or ligand mutations and modifications, e.g., ligand analogues.

The monoclonal antibodies of the present invention are suitable for use in a kit. Such a kit may comprise a receptacle being compartmentalized to receive one or more containers such as vials, tubes and the like, such containers holding separate elements of the invention. For example, one container may contain a first antibody bound to an insoluble or partly soluble carrier. A second container may contain soluble, detectably-labeled second antibody, in lyophilized form or in solution. The receptacle may also contain a third container holding a detectably labeled third antibody in lyophilized form or in solution. A kit of this nature can be used in the sandwich assay of the invention.

Without further elaboration, it is believed that one skilled in the art can, using the preceding description, utilize the present invention to its fullest extent. The following examples are merely illustrative and not limitative of the remainder of the disclosure in any way whatsoever.

EXAMPLE 1

Immunization and Monoclonal Antibody Preparation

Monoclonal antibodies were prepared by immunizing BALB/c mice intraperitoneally with $10^7$ 32D cell transfectants expressing the human α PDGFR, at ten day intervals. Mouse sera was titered against the baculovirus expressed human α PDGF receptor by solid phase ELISA and immunorecognition confirmed by immunoprecipitation analysis. Spleens from the mice producing the highest antibody titer against the α PDGFR were fused with Sp2/0 myeloma cells. Hybridomas secreting immunoglobulins directed against the α PDGFR were selected by ELISA and cloned by limiting dilution. Ascites fluid or hybridoma supernatant was purified by Protein A Sepharose chromatography. Monoclonal antibody IgG was quantitated by absorbance at 280 nm assuming an extinction coefficient of 1.35. Isotype analysis demonstrated that αRl was an IgG2a.

EXAMPLE 2

Immunoprecipitation and ELISA

Human α PDGFR expressed in baculovirus and constitutively phosphorylated on tyrosine was purified by immunoaffinity chromatography using a PY20 agarose immunoaffinity column. Jensen, R. A., et al. *Biochemistry* (in press). Briefly, cells were harvested by centrifugation from a 500 ml spinner culture. A crude membrane fraction was made and divided into four aliquots. Each aliquot was processed by solubilization in 10 mM Tris pH 7.4/ 50 mM NaCl/0.5 mM EDTA/0.2% TX100, and the insoluble debris removed by low speed centrifugation. The solubilized material was batch loaded onto a PY20 agarose column overnight, washed extensively, then eluted with 10 mM phenyl phosphate (Sigma). α PDGFR was purified to over 95% homogeneity as assayed by silver staining and confirmed by Western blotting.

For immunoprecipitation analysis, 50 ng of affinity purified tyrosine phosphorylated PDGFR was incubated for 4 hours with 33 nM αRl in PBS/1%BSA/0.1% TX100. Then, 100 μl of 1:1 slurry of PA Sepharose CL4B was added for 1 hour and vigorously shaken. The immunocomplex was washed three times with PBS 0.1% TX100. The pelleted complex was solubilized in SDS running buffer/100 mM DTT, repelleted, and the supernatant loaded on a 7% SDS polyacrylamide gel. Phosphorylated α PDGFR was detected by Western blotting and probing with antiphosphotyrosine. For ELISA analysis, 20 ng of purified receptor was added to each well of a Falcon 3912 flexible assay plate and the assay performed essentially as described in LaRochelle, et al. *Mol. Cell. Biol.* 9: 3538–3542 (1989). Polyclonal antibodies to α PDGFR residues 959–973 (anti-PR1) or residues 1074–1089 (anti-PR2), used here as positive controls also have been previously described in Matsui, et al., *Science* 243: 800–804 (1989) and Jensen, R. A., et al. *Biochemistry* (in press).

Figure 1A:
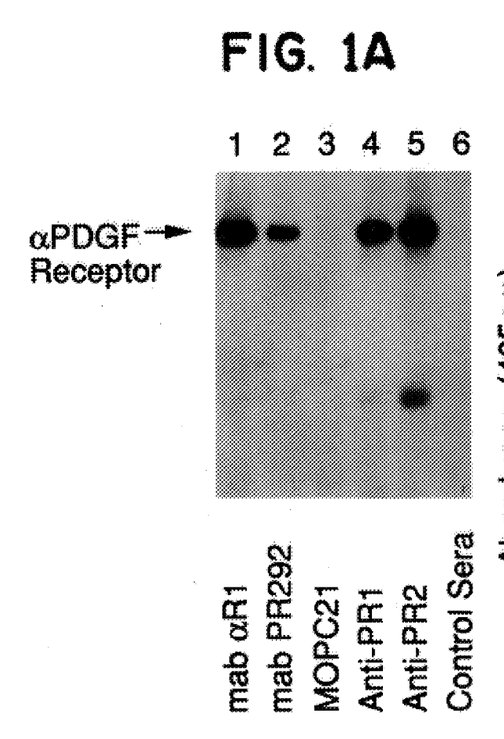

As shown in FIG. 1A, α PDGFR mab 1 (αR1) readily immunoprecipitated the baculovirus recombinant human α PDGFR which was recognized to a lesser extent by PR292, a commercially available mab. The specificity of its immunoreactivity was confirmed using antisera to α PDGFR peptides 959–973 (anti-PR1) or 1074–1089 (anti-PR2). Under the same conditions, neither control mab MOPC21 nor normal rabbit sera immunoprecipitated the α PDGFR. Moreover, αRl failed to recognize the human β PDGFR (data not shown), further demonstrating its α PDGFR specificity and the lack of epitope conservation between these two related receptor molecules. Since baculovirus expressed proteins are not terminally glycosylated, αRl recognition of the α PDGFR appears to be independent of its terminal glycosylation. Jensen, R. A., et al. *Biochemistry* (in press).

Figure 1B:
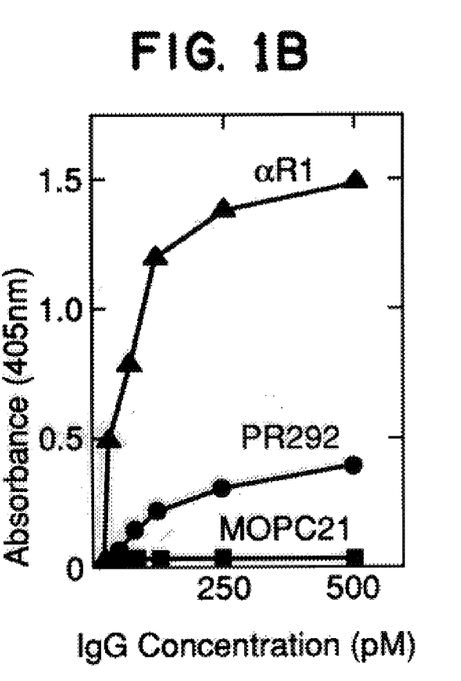

In order to more precisely characterize the relative affinity of αRl and PR292, these monoclonal antibodies were analyzed by ELISA using purified recombinant human α PDGFR (FIG. 1B). Mab αRl demonstrated saturable binding to the α PDGFR and possessed a half-maximal binding affinity of 50 pM. Mab PR292 bound with a slightly lower half-maximal binding affinity of 75 pM. Neither monoclonal antibody bound the β PDGFR in the solid phase ELISA confirming the results of immunoprecipitation studies (data not shown).

EXAMPLE 3

Species Recognition by Mab αRl

Immunoprecipitations were performed as described. Cell lines used in this study were D17 (dog), BHK (hamster), rab9 (rabbit), AG1523 (human), HFSSV (monkey), CV1 (rat), NIH 3T3 (mouse), cat (NIGMS Cell Repository #GM06207), and pig fibroblasts (gift of Dr. Timothy Fleming). Cell lines were starved eighteen hours in serum free media (DMEM), then triggered with 250 ng/ml PDGF BB. Cells were harvested, solubilized in 1% TX-100, and the lysate cleared by centrifugation. The supernatant was immunoprecipitated with 5 μg of αR1 or 5 μl of antipeptide sera as described. After immunoprecipitation, proteins were loaded onto a 7% SDS polyacrylamide gel. Separated proteins were transferred to Immobilon-P and probed with an antibody to phosphotyrosine. Bound primary antibody was detected with iodinated Protein A.

Figure 2:
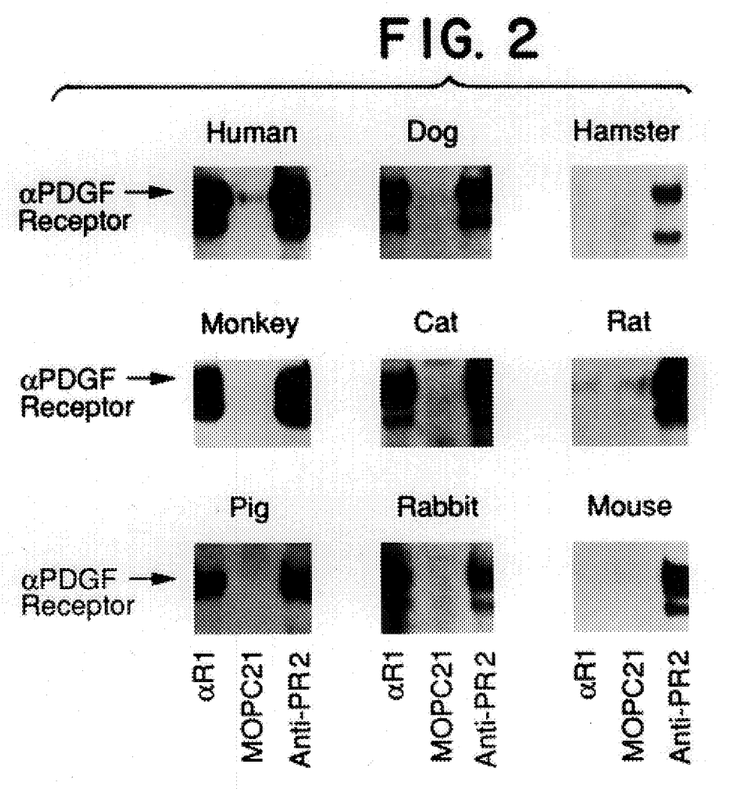

As shown in FIG. 2, αRl recognized human, monkey, pig, dog, cat, and rabbit α PDGFR to a similar extent as anti-PR2. However, αRl failed to immunoprecipitate hamster, rat, or mouse α PDGFRs which were readily detectable by anti-PR2. Anti-PR1 also immunoprecipitated α PDGFRs in the entire panel of cell lines (data not shown). These results indicated that αRl recognized an epitope of the α PDGFR distinct from that detected by anti-PR1 or anti-PR2.

EXAMPLE 4

Mab αRl Recognizes Extracellular Determinants of the α PDGFR

In order to test whether αRl recognized an extracellular or intracellular epitope, applicants performed flow cytometry on intact 32D cell transfectants expressing the α PDGFR. These cells have been shown to orient PDGFRs in a normal fashion such that their ligand binding domains are accessible at the cell surface. Matsui et al. *Science* 243: 800–804 (1989).

Flow cytometry was performed as described in Ashmun et al., *Blood* 73: 827–837 (1989). Briefly, cells were incubated with αR1 for 30 minutes. Bound primary antibody was detected with fluorescein-conjugated goat anti-mouse IgG. Cells were then processed on a FACSCAN analyzer (Becton Dickenson).

Figure 3:
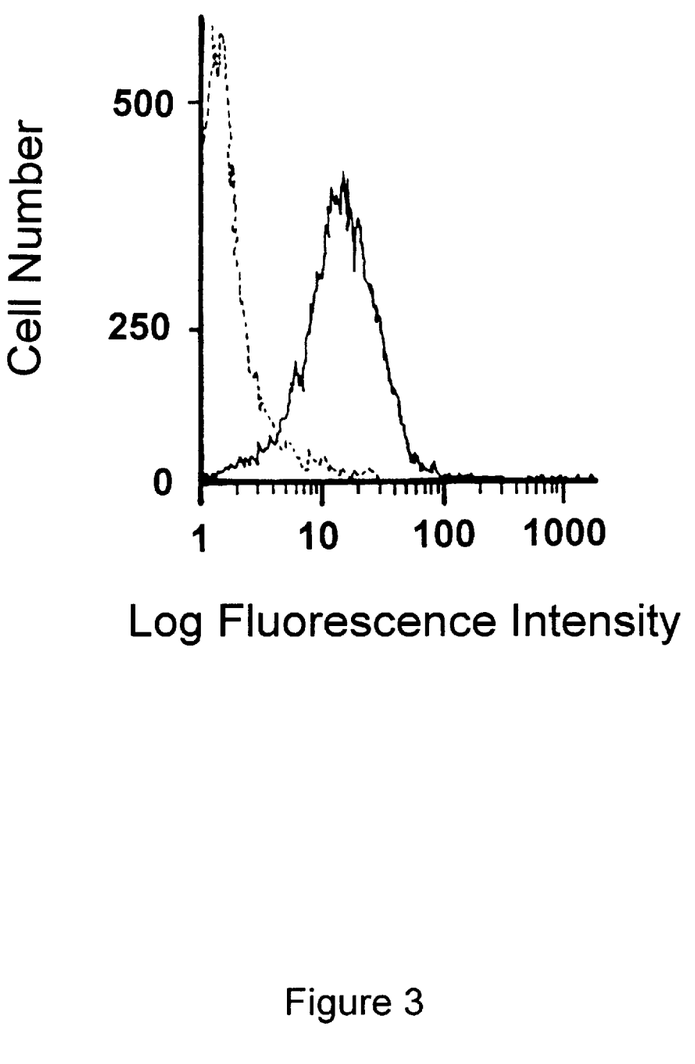
FIG. 3 shows flow cytometric assay of mab αR1 binding to intact 32D cell transfectants expressing the α PDGFR. 32D cell transfectants were incubated with mab αR1 (—) or control mab (- - - - -). Bound primary mab was detected with rabbit anti-mouse FITC as described in methods.

As shown in FIG. 3, αRl specifically recognized a PDGFR expressing 32D cells (32D αR) as indicated by a ten to one hundred-fold increase in fluorescence intensity compared to an isotype specific control monoclonal antibody. While PR292 also specifically recognized 32D αR, neither PR292 nor αRl recognized untransfected 32D cells or 32D transfectants containing the β PDGFR (data not shown). Recognition of the α PDGFR extracellular domain indicates that αRl recognized an epitope residing in the ligand binding domain of the receptor.

Some monoclonal antibodies which bind extracellular receptor domains have been shown to aggregate or cap receptors and subsequently induce their internalization. Sherr, et al. *Blood* 73: 1786–1793 (1989). Thus, it was investigated whether αR1 might cause down regulation of α PDGF receptors. Following αR1 incubation with the 32D-αR cells for 1 hour at 4° C. or 37° C., there was no decrease in surface immunofluorescence (data not shown). These results indicate that mab αR1 recognizes an external domain epitope whose binding does not induce α PDGFR internalization.

EXAMPLE 5

Biological Activities of αR1

Figure 4:
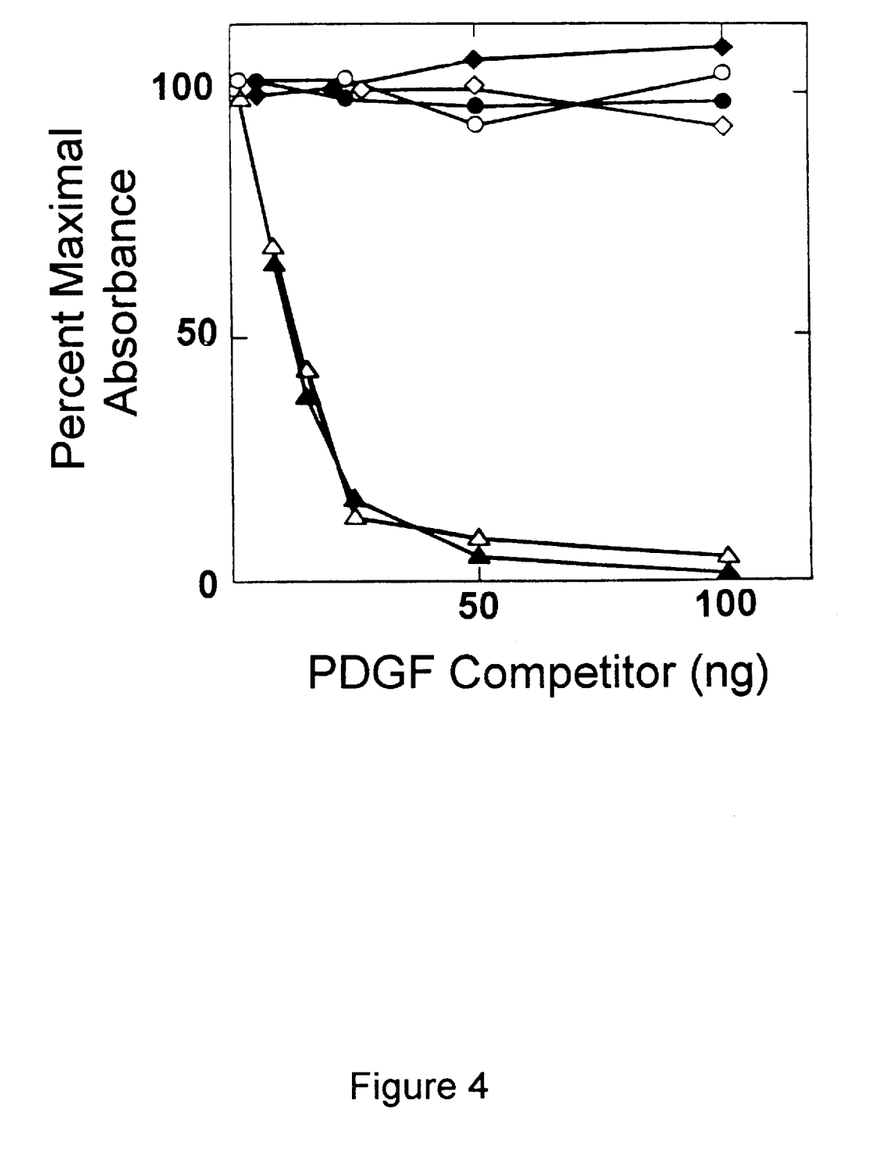
FIG. 4 shows PDGF AA or PDGF BB inhibition of antibody binding to the α PDGF receptor. PDGF AA (open symbols) or PDGF BB (closed symbols) were tested at the indicated quantity for their ability to inhibit mab αR1 (▲,Δ), mab PR292 (●,○), or anti-PR2 (♦,◊) binding to the α PDGF receptor.

The effects of αR1 on PDGF ligand binding and mitogenic stimulation were next investigated. To measure PDGF competition for αR1 recognition of the receptor, a solid phase ELISA type binding assay was utilized. Affinity purified α PDGFR (50 ng/well) was plated in a 96 well format as performed in the solid phase ELISA. Plates were blocked with PBS/4% BSA/0.02% azide for 30 minutes. PDGF AA or PDGF BB was added at the indicated concentration in PBS/1% BSA/0.05% Tween 20/0.02% azide. Next, αR1, αPR292, MOPC21 were added at 300 pM for 18 hours. Antipeptide antibodies was used at a dilution of 1/100. After washing four times with PBS/0.05% Tween 20/0.02% azide, either rabbit anti-mouse or goat anti-rabbit conjugated to alkaline phosphatase was used to detect bound primary antibody. After a two hour incubation, secondary antibody was removed by washing and 1 mg/ml alkaline phosphatase substrate 104 (Sigma) was added in 100 mM bicarbonate buffer/1 mM $MgC_{12}$ pH 9.8. The optical density was read at 405 nm. Maximal inhibition was defined as the difference between the optical density obtained with each antibody in the absence of PDGF competitor and that measured in the presence of excess PDGF (100 ng). As shown in FIG. 4, either PDGF AA or BB blocked α PDGFR detection of αR1 in the range of 25 to 250 ng/ml, but failed to block PR292, anti-PR1, or anti-PR2 recognition over the same concentration range. The similar efficiencies of PDGF AA or PDGF BB inhibition of mab αR1 binding suggested that both α PDGFR ligand binding domains spatially overlapped with the αR1 epitope.

Figure 5:
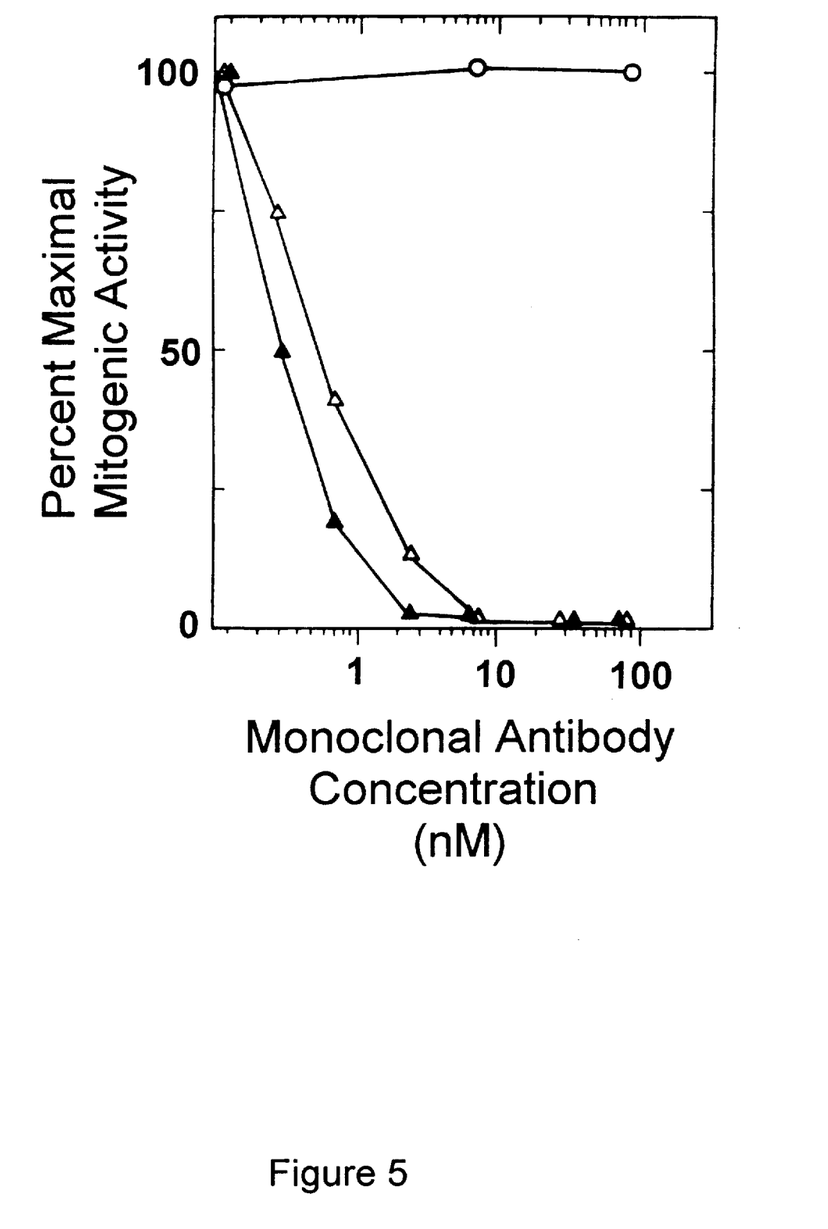
FIG. 5 shows mab αR1 inhibition of PDGF induced mitogenic activity using 32D αR transfectants. Varying concentrations of mab αR1 were tested for their ability to inhibit $^3$H-thymidine uptake of 32D αR after growth stimulation with PDGF AA (Δ), PDGF BB (▲), or IL-3 (○).
Figure 6A:
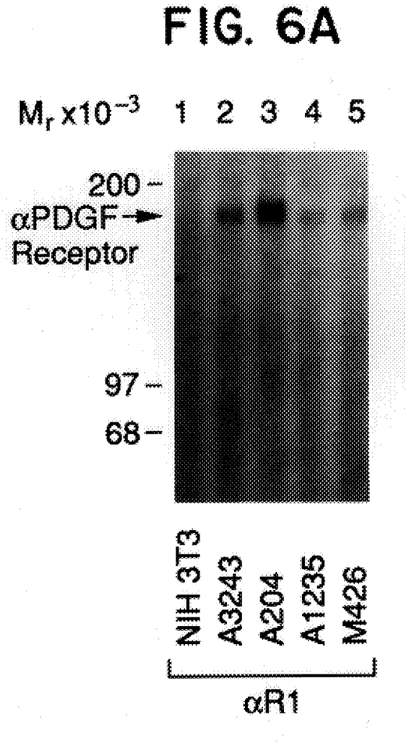
Figure 6B:
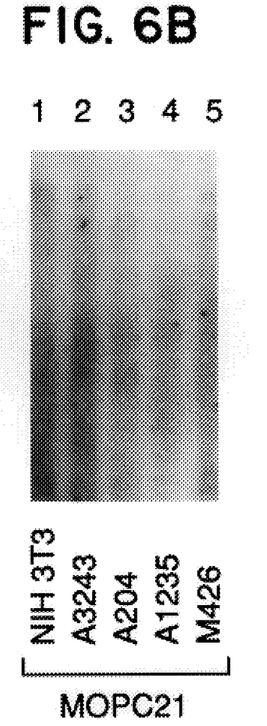

Because PDGF blocked αR1 binding to the α PDGFR, applicants tested whether αR1 inhibited PDGF AA or PDGF BB induced DNA synthesis in 32D αR cells triggered with either ligand. As shown in FIG. 5, 100 ng/ml PDGF AA or PDGF BB were inhibited half-maximally at αR1 concentrations of around 400 and 670 pM respectively. At concentrations between 5 and 50 nM, αR1 totally abolished $^3$H-thymidine uptake induced by either PDGF, but not by IL-3 further demonstrating the specificity of αR1. Under the same conditions, a control monoclonal antibody showed no inhibition of PDGF AA or PDGF BB induced $^3$H-thymidine uptake and PR292 inhibited only weakly. All of these results indicated that αR1 is a potent and specific inhibitor of α PDGFR mediated responses.

EXAMPLE 6

αR1 Abrogates Autocrine Proliferation of 32D Cell Transfectants Co-expressing PDGF AA or PDGF BB and the α PDGFR Supertransfection of 32D αR with expression vectors for PDGF AA or PDGF BB results in the creation of an autocrine loop. Such cell lines exhibit IL-3 independent proliferation in vivo and are malignant in vivo. See Heidaran et al., *Mol. Cell Biol.* 11: 134–142 (1991). Because these cell lines provide a model for study of PDGF autocrine growth stimulation of the α PDGFR, applicants tested whether αR1 was a specific antagonist of their proliferation.

Specifically, 32D transfectants ($2\times10^5$ cells/ml) expressing the α PDGFR were washed in PBS and triggered overnight in RPMI 1640 growth medium with PDGF AA or PDGF BB and varying concentrations of αR1 or a control mab. The next day, cells were incubated with $^3$H-thymidine (0.5 μCi) for five hours, washed, and harvested onto glass filters with an automatic harvester (Skatron). Incorporated tritium was counted in a Beckman 5500 scintillation counter.

In order to determine whether αR1 blocked autocrine stimulation, 32D transfectants expressing the α PDGFR and either PDGF AA or PDGF BB ($5\times10^4$ cells/ml) were incubated in RPMI growth medium with or without 330 pM αR1 for 48 hrs. Next, the cells were incubated with $^3$H-thymidine for five hours and processed as described above. A control monoclonal antibody showed no inhibition of PDGF/α PDGFR autocrine growth stimulation.

As shown in FIG. 7, αR1 specifically inhibited the proliferation of 32D cell transfectants coexpressing the α PDGFR and either PDGF AA or PDGF BB by greater than 50%. The same antibody showed no inhibition of 32D cells grown in the presence of exogenous IL-3 nor did a control monoclonal antibody cause any inhibition of PDGF autocrine growth stimulation of these cells. Thus, αR1 inhibited α PDGFR autocrine proliferation.

EXAMPLE 7

32D αPDGFR Binding Assay

For inhibition of $^{125}$I-PDGF AA or PDGF BB binding to 32DαR (mouse hematopoetic cell line that when transplanted into mice form tumors), transfectants were harvested by centrifugation, washed in DMEM, gently resuspended in HB binding buffer (DMEM/25 mM HEPES pH 7.4/1 mg/ml BSA), and maintained at 37° C. Next, $1.2\times10^6$ 32DαR cells, monoclonal αR1 at the indicated concentration, and 2 ng of iodinated PDGF AA or PDGF BB were incubated in HB buffer for 2 hours at 16° C. After 1 hour, the cell suspension was layered onto 300 μl of chilled oil mix (n-butyl phthalate (Fischer)/Bis (2-ethylhexyl) phthalate (Kodak) 1.5:1). Cells were centrifuged in an Eppendorf microfuge at 10K for 10 minutes at 4° C. The cell pellet was removed and counted in a Beckman 5500 gamma counter. Specific PDGF binding was calulated by subtraction of background binding, defined as counts remaining after incubation with a hundred-fold excess of unlabeled PDGF.

TABLE 1

| 32D Cell Line | $^3$H-Thymidine Uptake (CPM × $10^3$) | | Percent Inhibition |
|---|---|---|---|
|  | Uptake | +αR1 |  |
| 32D alone | 244 | 245 | 0 |
| 23.16 αR + AA | 315 | 146 | 54 |
| 39.12 αR + BB | 126 | 64 | 49 |
| 39.ωR βR + BB | 431 | 435 | 0 |

What is claimed is:

1. An assay for the detection of α Platelet-Derived Growth Factor (PDGF) receptors in a sample, comprising contacting said sample with a monoclonal antibody or fragment thereof and detecting the binding of said α PDGF receptor in said sample with said monoclonal antibody or fragment thereof, wherein said monoclonal antibody or fragment thereof is labelled for detection and specifically binds to an epitope on α PDGF receptor, inhibits PDGF binding with PDGF receptor, antagonizes PDGF and does not bind β PDGF receptor.

2. A kit for determining the presence of α Platelet-Derived Growth Factor (PDGF) receptor in a sample, comprising a container containing the monoclonal antibody or fragment thereof and a second container containing a means for detecting the presence of said α PDGF receptor in a sample, wherein said monoclonal antibody or fragment thereof specifically binds to an epitope on α PDGF receptor, inhibits PDGF binding with PDGF receptor, antagonizes PDGF and does not bind β PDGF receptor.

* * * * *